United States Patent [19]

Morris et al.

[11] Patent Number: 5,173,434
[45] Date of Patent: Dec. 22, 1992

[54] MEASUREMENT OF COLOR REACTIONS BY MONITORING A CHANGE OF FLUORESCENCE

[75] Inventors: Roger J. Morris, Sacramento; Shoshana Bascomb, Davis; Carolyn S. Olson, Sacramento, all of Calif.

[73] Assignee: Baxter Diagnostics Inc., Deerfield, Ill.

[21] Appl. No.: 609,278

[22] Filed: Nov. 5, 1990

[51] Int. Cl.[5] ............................................. G01N 21/76
[52] U.S. Cl. .................................... 436/172; 436/501; 436/537; 436/800; 250/458.1; 250/461.1
[58] Field of Search ............... 436/172, 501, 537, 800; 250/458.1, 461.1

[56] References Cited

U.S. PATENT DOCUMENTS

| Re. 31,879 | 5/1985 | Lubbers et al. | |
| 4,495,293 | 1/1985 | Shaffar | 436/172 |
| 4,653,907 | 3/1987 | Freundlich | |
| 4,772,558 | 9/1988 | Hammann | |
| 4,798,788 | 1/1989 | Sands | |
| 4,857,472 | 8/1989 | Wolfbeis | 436/172 |
| 4,945,060 | 7/1990 | Turner et al. | |

FOREIGN PATENT DOCUMENTS

| 0091837 | 10/1983 | European Pat. Off. |
| 0124193 | 11/1984 | European Pat. Off. |
| 0171158 | 2/1986 | European Pat. Off. |
| 1601689 | 11/1981 | United Kingdom |

OTHER PUBLICATIONS

Ando et al., Pyruvate as a Fluorescence Quencher: A New Spectroscopic Assay for Pyruvate Reactions, Anal. Bio. 129, 170-175 (1983).
Shoshana Bascomb, Enzyme Tests in Bacterial Identification, Method in Microbiology, 19: 105 (1987).
Blumberg et al., Hemoglobin Determined in 15 μL of Whole blood by "Front-Face" Fluorometry, Clin. Chem. 26/3, 409-413 (1980).
Carmel et al., An Intramolecularly Quenched Fluorescent Tripeptide as a Flurogenic Substrate of Angiotensin-I-Converting Enzyme and of Bacterial Dipeptidyl Carboxypeptidase, Eur. J. Biochem., 87 265-273 (1978).
Carmel et al., Intramolecularly-Quenched Fluorescent Tripeptide as a Fluorogenic Substrates of Leucine Aminopeptidase and Inhibitors of Clostridial Aminopeptidase, Eur. J. biochem., 73, 617-625 (1977).
Fleminger et al., Fluorogenic Substrates for Bacterial Aminopeptidase P and Its Analogs Detected in Human Serum and Calf Lung, Eur. J. Biochem., 125, 609-615 (1982).
Florentin et al, A Highly Sensitive Fluorometric Assay for "Enkephalinase," a Neutral Metalloendopeptidase That Releases Tyrosine-Glycine-Glycine from Enkephalins, Anal. Biochem. 141, 62-69 (1984).
Rhines et al., Simplex Optimization of a Fiber-Optic Ammonia Sensor Based on Multiple Indicators, Anal. Chem., 60, 76-81 (1988).
Wolfbeis et al., Fibre-Optic Fluorescing Sensor for Ammonia, Anal. Chimica Acta, 185, 321-327 (1986).
Yaron et al., Intramolecularly Quenched Fluorogenic Substrates for Hydrolytic Enzymes, Anal. biochem., 95, 228-235 (1979).

Primary Examiner—James C. Housel
Assistant Examiner—Maureen M. Wallenhorst
Attorney, Agent, or Firm—Kent Barta; Mark J. Buonaiuto; Paul C. Flattery

[57] ABSTRACT

A process to determine the concentration of any substance in a colorimetric, turbidimetric or nephelometric reaction using a fluorometric detector to measure fluorescence intensity. In particular, a change in color can be monitored by observing the measurement of fluorescence intensity of a fluorophore in an inert matrix. The absorption spectrum of the chromophore may overlap the excitation and/or emission spectrum of the fluorophore, thereby allowing the change in fluorescence to be related to the intensity of color in the reaction and thus related to the quantity of the substance of interest.

4 Claims, 9 Drawing Sheets

MEASUREMENT OF COLOR REACTIONS BY MONITORING A CHANGE OF FLUORESCENCE

FIELD OF THE INVENTION

This invention relates to a method to detect or determine the presence or determine the concentration of a chromophore in a solution by its regulation of light reaching a fluorophore encapsulated in a chemically inert light transparent matrix.

BACKGROUND OF THE INVENTION

Chemical and enzymatic reactions are used to detect or quantitate the presence of certain substances in microbiological or other assays. Many of these tests rely on the development or change of color or fluorescence to indicate the presence or quantity of the substance of interest.

There are many examples of reactions used in Microbiology that rely on a color change. Bascomb, *Enzyme Tests in Bacterial Identification*, Meth. Microbiol. 19, 105 (1987). For example, a variety of organisms can be classified in large part by their pattern of fermentation, oxidation or assimilation of carbon sources. Fermentation of carbohydrates results in the production of acid which causes a decrease in pH. This drop in pH can be easily detected by including a pH indicator like bromothymol blue or phenol red. With both indicators, acid conditions representing the fermentation of a particular carbohydrate result in a yellow color (changing from blue-green for bromothymol blue or pink/red for phenol red). The same approach can be adopted for a variety of carbohydrates, ranging from monosaccharides like glucose to polysaccharides like inulin. In an analogous fashion, increasing pH can also be followed. Assays for detecting the presence of decarboxylase and urease, and the ability to use malonate are based on an increase in pH, as indicated by a color change in an indicator.

Another approach to determine if an organism can degrade a particular substrate, is to use a reagent which is capable of reacting with one or more of the intermediates or final products. For example, the detection of the reduction of nitrate to nitrite. If nitrite is formed, then a pink to deep red color will result when sulfanilic acid and alpha-napthylamine are added to the reaction mixture.

In contrast to the indirect detection of an enzymatic reaction illustrated by the nitrate/nitrite test, it is possible to use a synthetic analog of a natural substrate to directly indicate the presence of an enzyme. For example, methylene blue can be reduced under certain conditions by the action of reductase, resulting in a shift from blue to colorless. In another test, the oxidase assay relies on the interaction of cytochrome oxidase with N,N,N',N'-tetramethyl-p-phenylenediamine producing a blue color.

Another example is the ability of microorganisms to degrade sulfur-containing amino acids as indicated by the production of $H_2S$. Typically, the organism is incubated with a high concentration of a sulfur-containing substrate (e.g. cysteine, cystine) in an acid environment. The production of $H_2S$ is indicated by the formation of a black precipitate in the presence of ferric ammonium citrate.

Enzymes can usually act on more than one substrate. This allows for the use of synthetic enzyme substrates for the detection of enzyme activities. Synthetic substrates contain a metabolic moiety conjugated with a chromatic or fluorescent moiety. The conjugated molecule usually has a different absorption and/or emission spectrum from the unconjugated form. Moreover, the unconjugated chromatic or fluorescent moiety shows a considerably higher absorption or fluorescence coefficients than those of the conjugated molecule. This allows the measurement of small amounts of products of enzyme activities in the presence of the large amounts of conjugated substrate required for maximal enzyme activity. An example of a synthetic enzyme substrate is o-nitro-phenol-$\beta$-galactopyranoside used for the detection of activity of the enzyme $\beta$-galactosidase. The conjugated substrate is colorless. The $\beta$-galactosidase enzyme hydrolyzes the substrate to yield $\beta$-galactosidase and o-nitro phenol. o-nitro-phenol absorbs strongly at 405 nm, and its release can be measured by the increase in absorbance at that wavelength. Bascomb, *Enzyme Tests in Bacterial Identification*, Meth. Microbiol. 19, 105 (1987), reviewed the synthetic moieties used for enzyme substrates and the enzymatic activities measurable using this principle.

Presently, the monitoring of color or color end-product in chemical and microbial reactions is usually achieved in either of two ways; 1) the detection of color or color end-product can be achieved by visual observation and estimated qualitatively, or 2) the detection of color end-products or loss of color can be achieved by measuring the intensity of color instrumentally. Spectrophotometers that measure light absorbance are commonly used for this purpose. When measuring the concentration of a number of substances it is advantageous to use one instrument or one principle of measurement, otherwise cost is increased.

Although the use of colorimetric reactions is widespread there are limitations, especially in the sensitivity of detection. In order to improve sensitivity and, in the case of identification of microorganisms, thereby to decrease the time required to obtain a result, fluorescence-based methods frequently are used. Unfortunately, it may not be possible to develop a fluorescent equivalent to every assay. Additionally, the fluorescent reagents themselves may be highly toxic and therefore difficult to commercialize.

In such cases one might need to measure activities of some enzymes fluorometrically, the others colorimetrically. However, most instruments are suited to measure either absorbance or fluroescence, and very few can be used to measure both.

The general principle of fluorescence quenching has been accepted as a way to detect or determine enzymatic or chemical reactions. For example, Fleminger et al. synthesized intramolecularly quenched fluorogenic substrates for the assay of bacterial aminopeptidase P. Fleminger et al., *Fluorogenic Substrates for Bacterial Aminopeptidase P and its Analogs Detected in Human Serum and Calf Lung*, Eur. J. Biochem. 125, 609 (1982). In this case, the fluorescence of the aminobenzoyl group is quenched by the presence of a nitrophenylalanyl group. When the enzyme is present, the nitrophenylalanyl group is cleaved, with a concomitant increase in the sample's fluorescence. A variety of enzymes have been assayed by this type of procedure, including hydrolytic enzymes, other amino- and carboxypeptidases and an endopeptidase. Yaron et al., *Intramolecularly Quenched Fluorogenic Substrates for Hydrolytic Enzymes*, Anal. Biochem. 95, 228 (1979);

Carmel et al., *Intramolecularly- Quenched Fluorescent Peptides as Fluorogenic Substrates of Leucine Aminopeptidase and Inhibitors of Clostridial Aminopeptidase*, Eur. J. Biochem. 73, 617 (1977); Carmel et al., *An Intramolecularly Quenched Fluorescent Tripeptide as a Fluorogenic Substrate of Angiotensin-I-Converting Enzyme and of Bacterial Dipeptidyl Carboxypeptidase*, Eur. J. Biochem. 87, 265 (1978); Florentin et al., *A Highly Sensitive Fluorometric Assay for "Enkephalinase", a Neutral Metalloendopeptidase that Releases Tyrosine-Glycine-Glycine from Enkephalins*, Anal. Biochem 141, 62 (1984). In each of the previous approaches, a synthetic substrate containing a quenching group and a fluorescing group was generated in order to detect the activity of the enzyme.

An alternative to this approach would involve the synthesis of a resonance energy transfer pair of fluorescing groups on a substrate molecule. In this method, cleavage by the enzyme of one of the groups would result in a decrease in fluorescence, since the critical distance would be exceeded, eliminating the transfer of energy. However, the previously discussed approaches are limited to specifically designed substrates.

Still another approach involves the estimation of a chromophore by fluorescence measurement. See W. Blumberg et al., *Hemoglobin Determined in Whole Blood "Front Face" Fluorometry*, Clin. Hemo. 26, 409 (1980). Blumberg disclosed an assay based on attenuation of fluorescence of a dye, whose excitation wavelengths overlap with the absorption wavelengths of the chromophore.

Subsequently, M. Shaffer, U.S. Pat. No. 4,495,293 (hereinafter Shaffer) filed a patent application disclosing a method to fluorometrically determine a ligand in an assay solution using conventional fluorometric techniques. In Shaffer the intensity of the fluorescence emitted by the assay solution is related to the change in transmissive properties of the assay solution produced by the interaction of the ligand to be determined and a reagent system capable of producing change in the transmissive properties of the assay solution in the presence of the ligand. More particularly, Shaffer discloses a method to monitor absorbance using a fluorophore in solution with the chromophore. In this method the fluorophore may interact with the assay cocktail and produce changes in fluorescence intensity which are unrelated to the change being measured. The selection of the fluorophores is also restricted, in that pH dependent or environment sensitive fluorophores cannot be utilized. Additionally, when the fluorophore is in solution, less than accurate measure of absorbance may be obtained because light is absorbed exponentially through the chromophore sample.

Similarly, Beggs & Sand, EPA 91,837 disclosed a solution based method for determination of tryptophan-deaminase activity by measuring the reduction in fluorescence in the presence of a chromophore produced by the interaction between indole pyruvic acid and metal ions using a fluorophore "whose fluorescence is capable of being quenched by the indole pyruvate-metal ion complex, the ions of the fluorophore being present throughout the incubation period".

Also, Sands, U.S. Pat. No. 4,798,788 discloses a process to detect a nitrate reducing microorganism by measuring reduction of fluorescence in solution by causing the diazotization of the fluorophore. In all these cases a specific fluorophore needs to be chosen for each test to ensure that it will fluoresce under the conditions of the test, e.g. only few fluorophores fluoresce at pH of less than 2.0.

Consequently, a need exists to develop a general process to detect or determine the concentration of any substance so that any fluorophore with the appropriate spectral characteristics may be employed. Additionally, a need exists to develop a process to maximize the amount of light detected in a fluorometric assay so that assay sensitivity can be increased.

SUMMARY OF THE INVENTION

The invention involves a process to detect or determine the concentration of a substance that directly or indirectly functions to change the light transmissive characteristics of a solution comprising: providing a light beam forming a transmission light path; providing a solution including said substance in said light path; the improvement comprising: positioning a fluorophore, in a chemically inert light transparent matrix, to intersect said light path; and detecting the change in fluorophore emission to determine the presence or concentration of said substance. The present invention involves a process to detect or determine the concentration of an unknown substance in a colorimetric, turbidimetric or nephelometric reaction using a fluorometric reader. A change in color, turbidity or light scattering can be monitored by observing the change in fluorescence of an inert fluorophore enclosed in a light transparent matrix. In particular, in a colorimetric reaction, this result can be achieved when the absorption spectrum of a chromophore overlaps the excitation and/or the emission spectrum of a fluorophore, thereby allowing the change in fluorescence to be related to the intensity of color in the reaction and consequently related to the quantity of the substance of interest. It should be noted that the spectrum is not limited to visible light.

This invention provides a method to use a fluorophore enclosed or embedded in a chemically inert matrix which is transparent at the wavelengths of interest. The fluorophore, positioned to intersect the transmission light path, indirectly monitors absorbance or changes in the absorbance of a chromophore. The use of a fluorophore enclosed or embedded in a matrix allows for the sequential influence of reaction components on the intensity of light detected.

The invention is also directed to a process to detect the presence or determine the concentration of a substance in solution using a chromogenic reagent that reacts with the substance or a compound related to the substance to form a chromogenic reaction product, the chromogenic reaction product having an absorption spectrum that overlaps the excitation and emission spectrum of a fluorophore, to regulate light reaching a fluorophore and a fluorescence detector comprising: providing a light beam forming a transmission light path; positioning a solution including the substance and the chromogenic reagent in the light path; positioning a fluorophore, with an excitation and emission spectrum that overlaps the absorptive spectrum of the chromogenic reaction produced, in a chemically inert light transmissive matrix, to intersect chromophore regulated light; and detecting the change in fluorophore emission to determine the presence or concentration of the substance.

Additionally, the invention is directed to a process to detect the presence or determine the concentration of a substance in solution using a chromogenic reagent that reacts with the substance or a compound related to the substance to form a chromogenic reaction product having an absorption spectrum that overlaps the emission spectrum of a fluorophore, to regulate light reaching a fluorophore and a fluorescence detector comprising: providing a light beam forming a transmission light path; positioning a fluorophore with an emission spectrum that overlaps the absorption spectrum of the chromogenic reaction product in a chemically inert light transmissive matrix, to intersect the light path; positioning a solution including the substance and the chromogenic reagent to intersect fluorophore regulated light; and detecting a change in fluorophore emission to determine the presence or concentration of the substance.

Additionally, the invention is directed to the process to detect the presence or determine the concentration of a substance in solution using a chromogenic reagent that reacts with the substance or a compound related to the substance to form a chromogenic reaction product having an absorption spectrum that overlaps the excitation spectrum of a fluorophore, to regulate light reaching a fluorophore and a fluorescence detector comprising: providing a light beam forming a transmission light path; positioning a solution including the substance and the chromophore in the light path; positioning a fluorophore with an excitation spectrum that overlaps the absorption spectrum of the chromophore, in a chemically inert light transmissive matrix, to intersect chromophore regulated light; and detecting a change in fluorophore emission to determine the presence or concentration of the substrate.

Additionally, this invention is related to a reaction chamber comprising a reaction chamber for use in the above described process comprising: a fluorophore enclosed or embedded in an inert light transmissive matrix having an emission and/or excitation spectrum that overlaps the absorption spectrum of a chromogenic reaction product, positioned in said reaction chamber to intersect said regulated light; and means for monitoring regulated light to detect the presence or determine the concentration of an unknown substance.

Principal advantages of this method are:
a) The capability of detecting and quantifying chromogenic reactions using a fluorometer. This dramatically increases the utility of the fluorometer since virtually all color reactions may be monitored indirectly using fluorescence. By careful selection of a fluorophore which has suitable excitation/emission profiles, an optimal test may easily be developed. Thus, a single instrument may be used for both fluorescence and absorbance measurements.
b) The isolation of fluorophore from the reaction mixture, in a chemically inert light transparent matrix, results in a source of fluorescence undisturbed by the environment of the assay cocktail.
c) Additionally, interrogation of the entire path length of the sample, i.e. the matrix, yields a more accurate representation of the sample, and, thus more sensitive assays.

Still, additionally, the invention relates to a kit to practice the above discussed methods.

DETAILED DESCRIPTION

Best Mode

In this approach, fluorescence from a fluorophore enclosed or embedded in a chemically inert light-transparent matrix, is modulated by a chromogenic reaction product formed by the interaction of chromogenic reagent and the substance of interest or another compound related to the substance. The assay is carried out in a reaction chamber where a fluorophore has been previously positioned to intersect the transmission light path. The reaction chamber may be a cuvette, a well on a microdilution or microwell plate or a blood culture bottle.

In a fluorometric based colorimetric assay the fluorescence intensity is regulated by changes in absorbance of an interfering chromophore. As a color change occurs the chromophoric material alters the amount of light reaching the fluorophore and/or the amount of emitted light reaching the detector. A determination of concentration and/or the presence of the chromophoric material is dependent on the interaction of a reagent and the substance to be measured, or the interaction of the chromogenic reagent and another compound related to the substance of interest. If the substance to be measured is present in the solution, then the chromophore absorbs light at a particular wavelength. Similarly, for assay systems not incorporating a chromophore the change in fluorescence can be affected by a turbidimetric or nepholometric change in the solution.

The requirements for a fluorometric based colormetric assay are based on the need for spectral overlap of the absorption spectrum of the chromogenic reaction product and the excitation and/or emission spectrum of the selected fluorophore. Sandwiching the chromophore (typically 8 mm) between the excitation light source and fluorophore matrix (typically 2 mm path) ensures complete interrogation of the entire path length of the chromogenic reaction product. This provides an accurate, proportional quantitative determination of absorbance. Monochromatic excitation and detection wavelengths are selected such that maximal absorbance changes are employed to achieve the concomitant changes in fluorescence intensity.

It is important to note that the fluorophore, distributed uniformly throughout the matrix, is completely isolated from the typically aqueous assay cocktail and is not a participant in any reaction. The immobilized fluorophore acts solely as a photon source capable of being attenuated or enhanced by the spectrally active chromophore. The matrix can be any inert support that is transparent at the wavelength of interest, e.g. liposome, beads, epoxy, etc. Similarly, a fluorescence filter in the reaction chamber can be used.

Figure 1A:
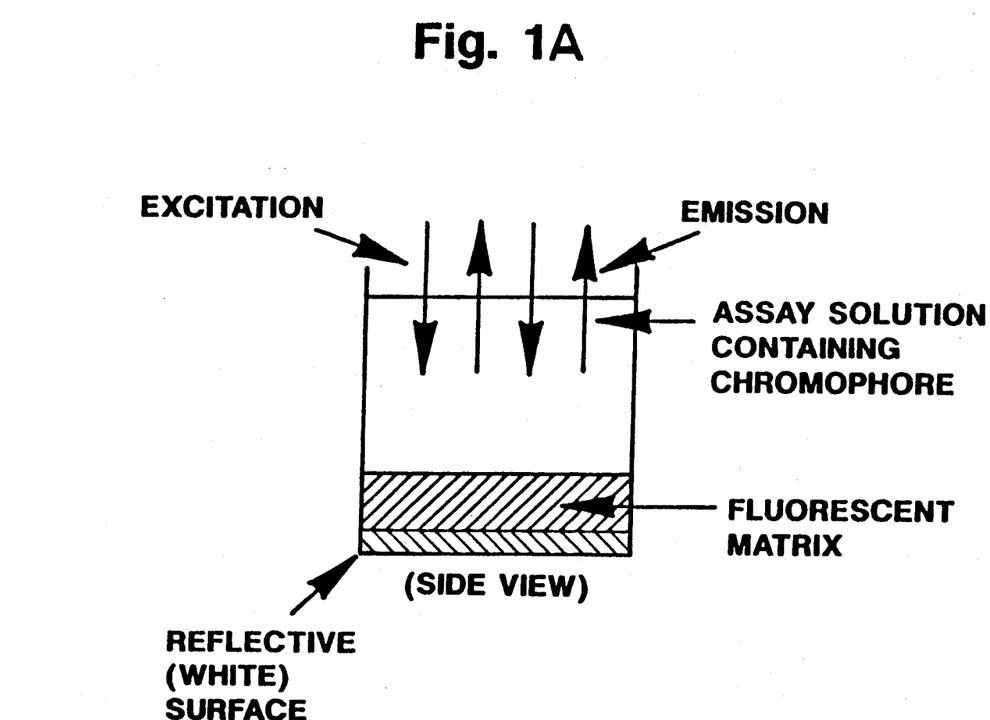
FIG. 1A shows regulation of excitation and/or emission light by a chromogenic reaction product, using front face fluorometry.
Figure 1B:
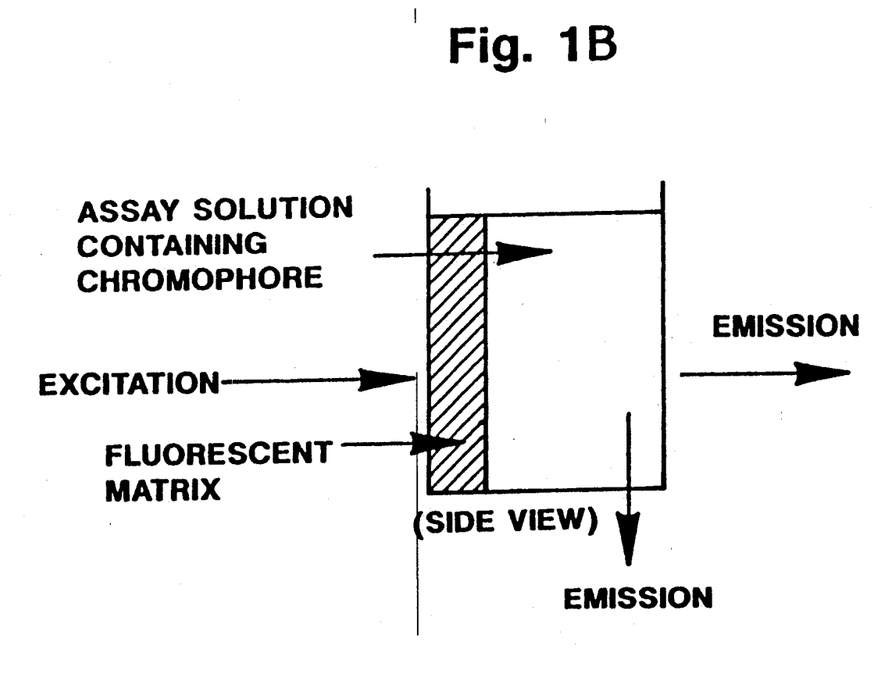
FIG. 1B shows the emission based absorbance measurement.
Figure 2:
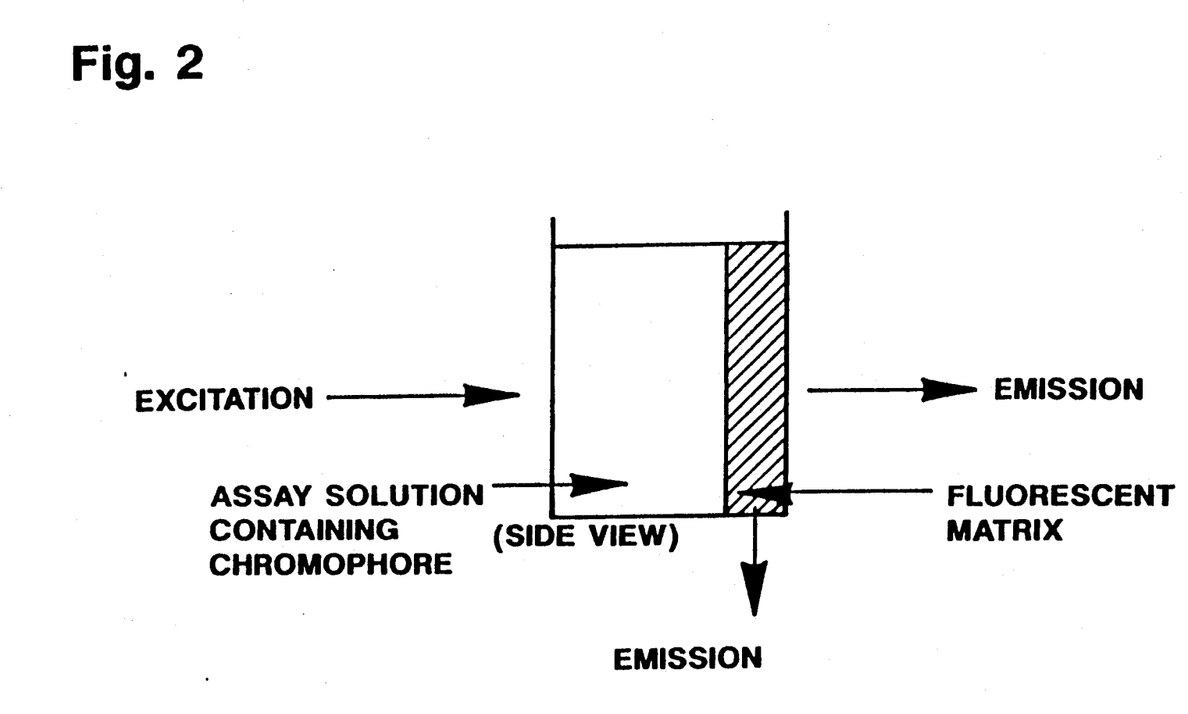
FIG. 2 shows an excitation based absorbance measurement.

Fluorescence may be monitored in several ways. Excitation and/or emission based absorbance measurement, i.e. front surface fluorometry, FIG. 1A, by an emission based absorbance measurement, i.e., conventional fluorometry, FIG. 1B and excitation based absorbance measurement, i.e. with conventional fluorometry, FIG. 2. As shown in FIG. 1B, Emission Based Absorbance Measurements, light in a transmission light path makes a single pass through the chromogenic reaction product exclusively regulating light; only absorption/fluorescence emission overlap is important. As shown in FIG. 2, positioning the chromogenic reaction product in the light path prior to the fluorescent matrix allows excitation control; in this situation only absorption/fluorescence excitation overlap is important. Front surface fluorescence measurement requires a double pass through the chromogenic reaction product; both excitation light and fluorescence emission may now be influenced simultaneously by the absorbing chromophore and thereby contribute to any delta change, which may offer a most favorable situation. See FIG. 1A, Excitation and/or Emission Based Absorbance Measurement. In this circumstance, spectral changes in two distinct regions corresponding to fluorophore excitation and emission, are brought to bear.

Alternatively, microorganisms that produce $CO_2$ can be detected by encapsulating the pH sensitive chromophore in a gas permeable proton impermeable matrix, if that layer is spectrally coupled to a chemically inert light transmissive matrix containing a pH insensitive fluorophore. Changes in fluorescence emission can be correlated with the presence of the microorganism in solution. In this case the fluorescence detector can be located below the embedded fluorophore.

In particular, components needed for the development of an assay using a fluorescence based absorbance measurement include:

a) Selection of the light transparent matrix and fluorophore

Although not essential for all applications a number of criteria must be considered in order to simplify material preparation and enhance stability and usefulness. These include:

1. Spectral transparency in the region of interest, typically 250 nm–700 nm.
2. Chemically inert and stable at pH extremes.
3. The absence of any destabilization interaction between immobilized fluorophore and the matrix environment over the long term.

Specifically, for an epoxy based system there are other characteristics that are required in addition to those mentioned above. These include:

1. Low viscosity to facilitate material dispensing.
2. Room temperature 25° C. (8 hour) cure or 65° C. high temperature (1 hour) cure.
3. The possession of adhesive properties to bind to a reaction vessel, typically the base.

To accommodate the above criteria, both uv curable and epoxy based adhesives may be used. The optimal material which displayed all of the above characteristics was Epotek TM 301 (Epoxy Technology Incorporated Inc. Billerica, Mass.).

The use of a fluorophore to indicate changes in chromogenic assays requires overlapping the excitation and/or emission spectrum of the fluorophore with the absorption spectrum of the chromophore or chromogenic reaction product. One very stable fluorescent dye was found to be 7-diethylamino-4-methylcoumarin, DM coumarin TM (Molecular Probes). This material has appropriate spectral requirements (excitation at 365 nm, emission at 450 nm) and a high quantum yield which makes it highly suitable for the chromophoric tests described below.

In the particular application described below, front surface fluorescence detection is utilized by the overhead monitoring of one reaction well on a multiple well. In this mode a white or alternate type of reflective panel may be used to enhance the amount of fluorescence collected.

The fluorometer used to develop these tests had single wavelength capability with limited spectral band pass excitation at (365 nm) and emission (450 nm). This light provides for exclusive interrogation of spectral regions which offer the greatest rate of change in absorbance for any given test.

Figure 3:
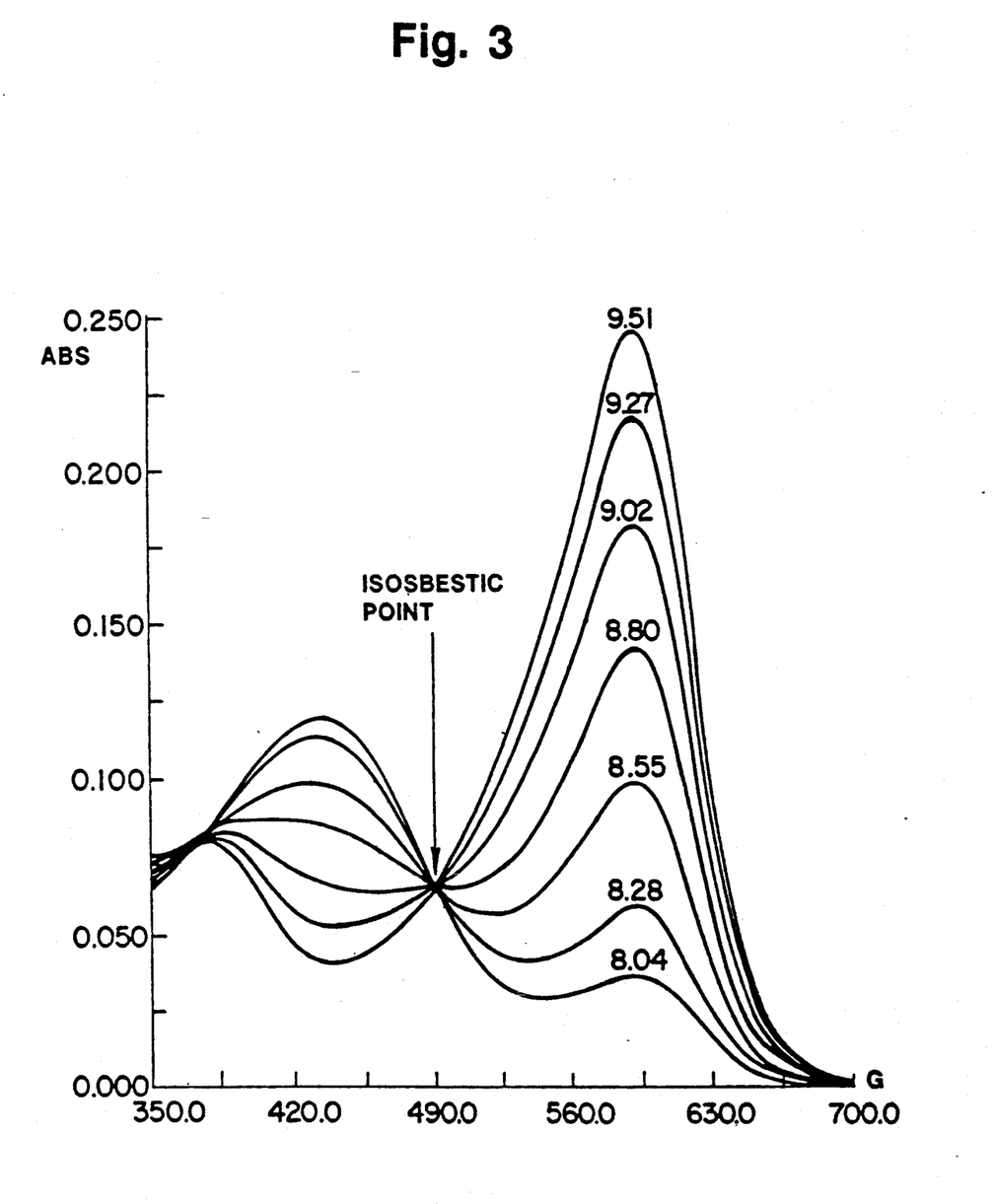
FIG. 3 shows the absorption spectrum for the dye xylenol blue when measured at different pHs and at the isosbestic point.

A series of spectrally overlapping fluorophores in a single matrix can be prepared which, when optically combined, cover a wide spectral range. This would provide a generic material which may be used in the uv, visible or infra red spectral regions for any chromophore test. In fact, fluorophores in the visible and infra red, where there is an abundance of light from low cost incandescent light sources, should offer significant improvements in the quality of data since the signal to noise ratio improves with increased light. Where possible, however, the use of a chromophore isosbestic point i.e., a spectral location within the chromophore spectral profile that is constant throughout a reaction, is selected as the chromophore absorbance wavelength, and is selected to provide an internal reference for any delta change measurements. See FIG. 3.

Quantitative determination of the concentration of a chromophore by means of a fluorescence based absorbance measurement is obtained by the following method:

This procedure outlines a general purpose approach to concentration measurement of a reaction mixture (the solution containing substance of interest and chromogenic reagent) product in solution, by positioning the chromogenic reaction product between a light source and an inert fluorescent matrix. A front surface excitation/emission detection fluorometer, as in FIG. 1A, permits an accurate estimate of chromophore, based on:

I) Attenuation of frontal, monochromatic, or limited spectral band pass, excitation light reaching the fluorophore by spectral overlap of the chromogenic reaction product absorption spectrum and the fluorophore excitation spectrum.

II) Attenuation of emitted fluorescence, reaching the frontal monochromatic, or limited spectral band pass detector, by spectral overlap of the chromophore absorption spectrum and the fluorophore emission spectrum.

The actual absorbance calculated will contain contributing absorbances from both of the above. A complete description of the specific example now follows, including the associated graph and calculations proving the experimental validity of this unique method.

1) Generation of a Confirmation Standard Curve Using a Spectrophotometer

A series of concentrations of a common, water soluble dye are prepared to yield an absorbance range of 0.1 to 1.0 based on the combined absorbances at the wavelengths of interest. For xylenol blue, spectral regulation (absorption) of light occurs between 400–600 nm. To accommodate the fluorophore discussed below, absorbance measurements were made vs. a water reference. Wavelengths corresponding to excitation and emission regions within the 400–600 nm were arbitrarily selected, namely 530 nm and 590 nm respectively. The absorbance values at these wavelengths were summed allowing a standard curve of combined absorbance vs. concentration, i.e. absorbance at 530 nm + absorbance 590 nm = absorbance sum.

A plot of absorbance vs. concentration, i.e.—a Beer Lambert plot, at relatively low concentrations will yield a straight line with an intercept of zero. A linear least squares fit of the data result in an accurate estimate of absorbance units per unit concentration. Should either wavelength absorbance of the unknown concentration of dye be specifically needed, the constant ratio of the excitation and emission wavelengths, determined spectrophotometrically, may be used.

In any fluorescence measurement it is critical that the fluorometer be capable of discriminating excitation and emission wavelengths of light (with sufficient Stokes shift) to ensure reflection or scattering problems do not interfere with this measurement.

Figure 4:
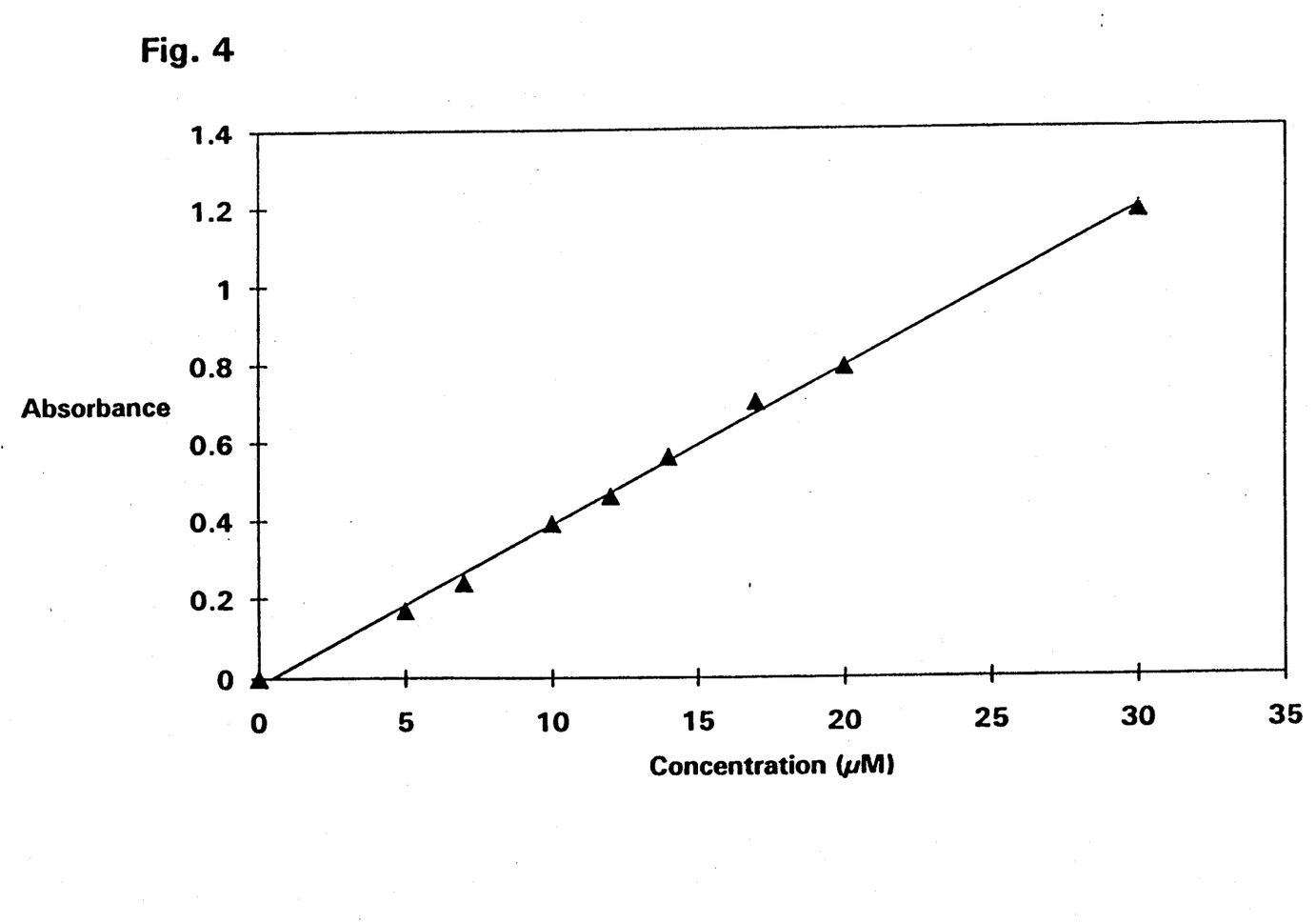
FIG. 4 shows data on the results of least squares curve fitting operations on the absorbance data.
Figure 5:
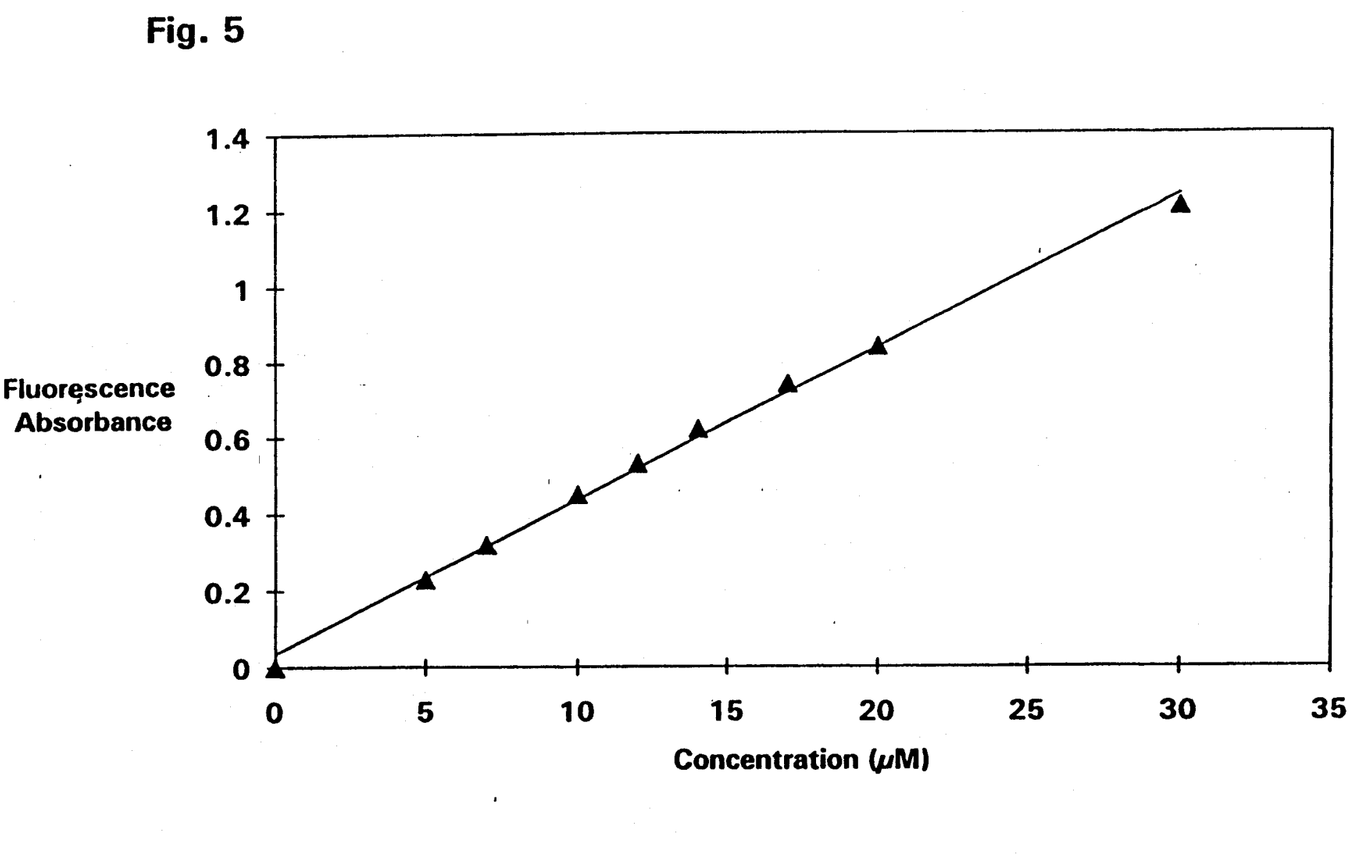
FIG. 5 shows data on the results of least squares curve fitting operations on the fluorescence based absorbance data.
Figure 6:
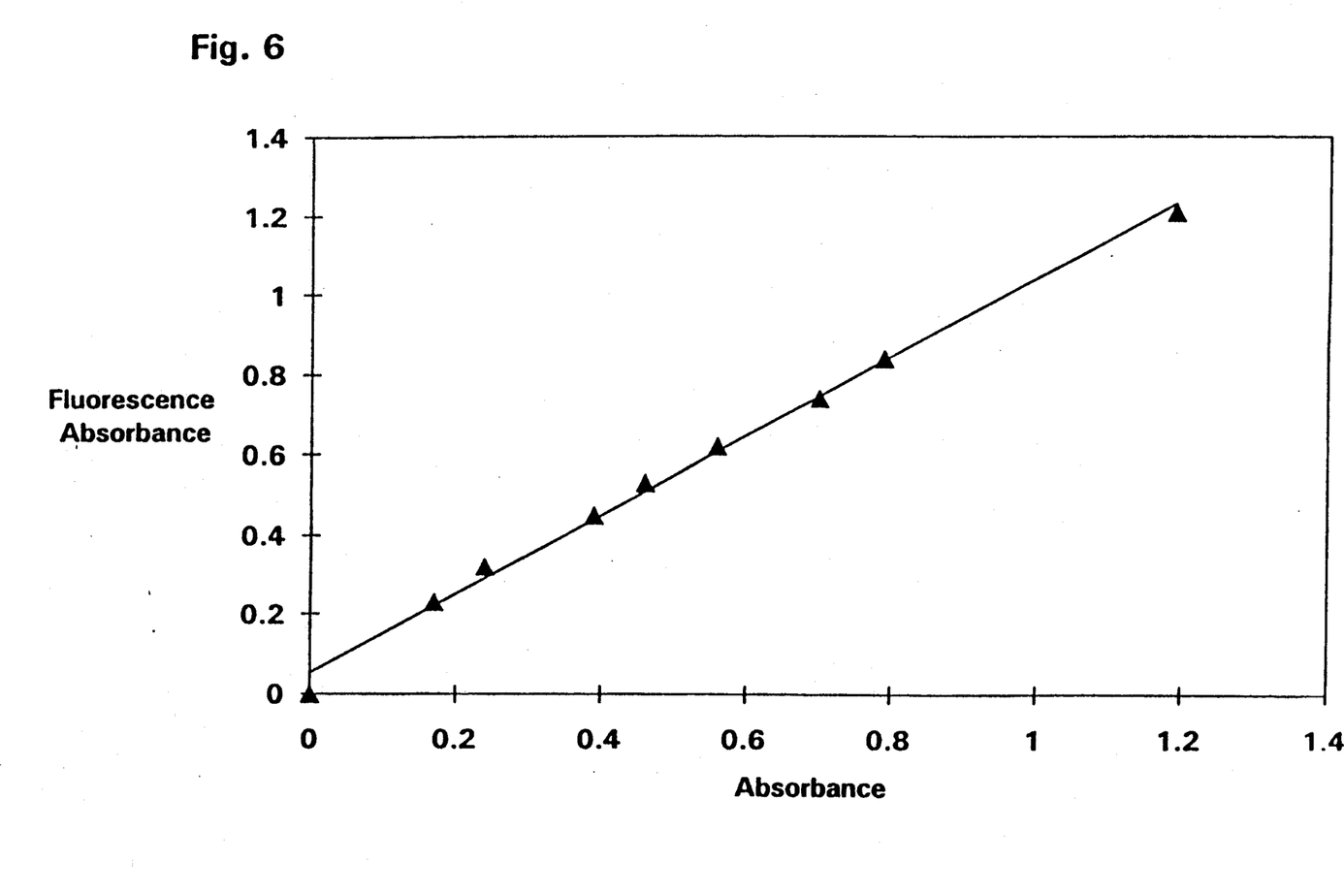
FIG. 6 shows data on the results of least square curve fitting operations on fluorescence based absorbance data vs. absorbance data.

FIGS. 4, 5 and 6 yield data on the results of least squares curve fitting operations on a) the absorbance data, b) the fluorescence based absorbance data and c) fluorescence based absorbance data vs. absorbance data.

Using $$\text{Abs(sum)} = E^* c^* d$$

where
E = combined extinction coefficients at both wavelengths
c = concentration
d = path length (1 cm).

E, a new extinction coefficient may be calculated and compared to the absorbance based fluorescence measurement described next.

2) Generation of an Absorbance Based Fluorescence Measurement Using a Fluorometer A suitable fluorophore, with excitation and emission spectral bands in the 400–600 nm region, is embedded in a transparent sheet of an acrylic matrix. A sheet of this matrix forms one side of a 1 cm cuvette which is positioned in a front surface fluorometer such that excitation light must traverse the entire 1 cm cuvette path before reaching the fluorophore; similarly emanating fluorescence must also pass through the 1 cm path before detection by the fluorometer.

Figure 7:
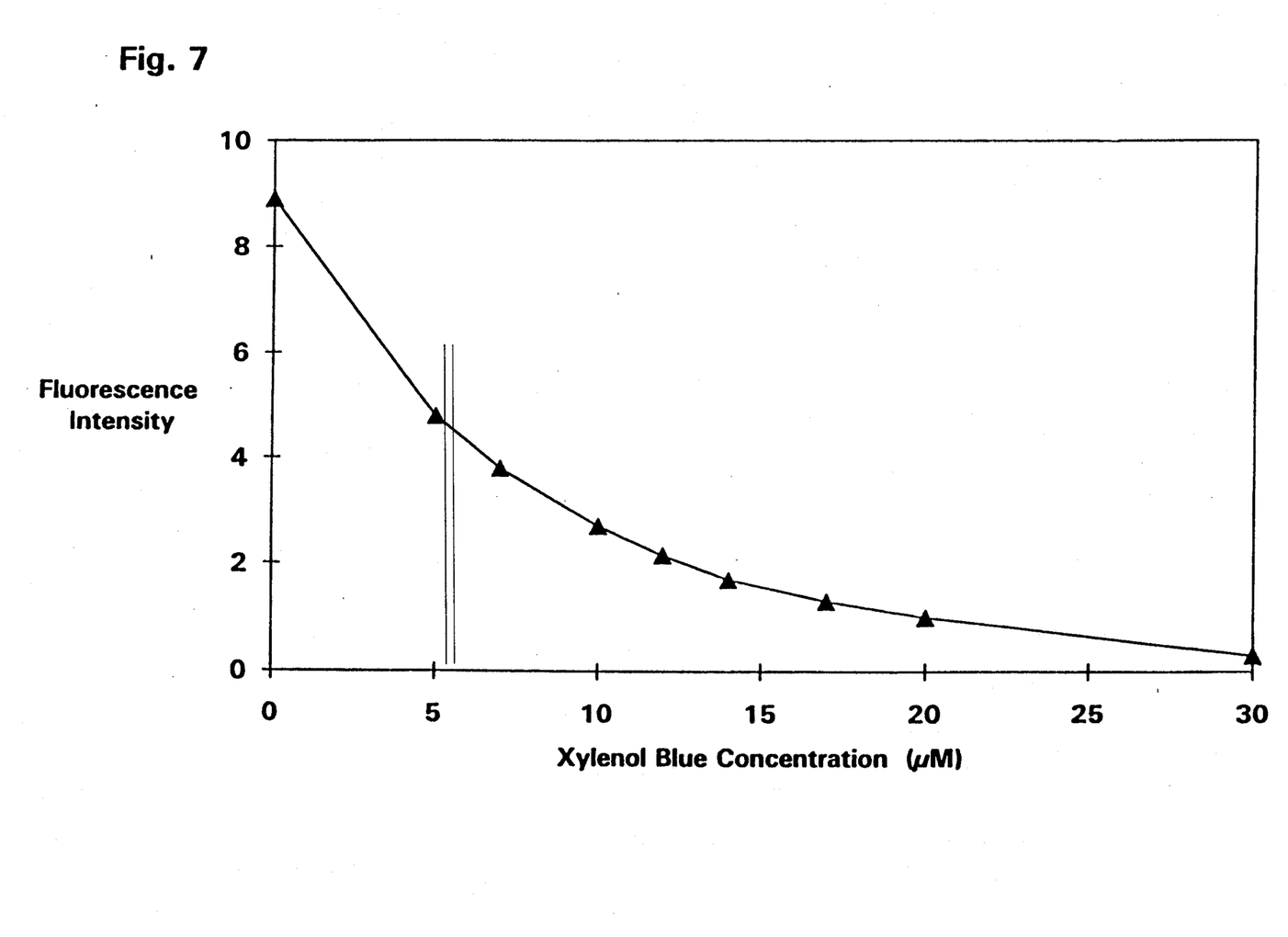
FIG. 7 shows fluorescence intensity vs. xylenol blue concentration.

Initially water is placed in the custom cuvette and an estimate of fluorescence intensity of the fluorophore (arbitrary units) is obtained. Next, the range of dye solutions are added separately to the cuvette and the fluorescence measured. The fluorescence intensities may now be used to determine the combined wavelength absorbance using $$\log 10(I_{Ref}/I_{Samp}) = \text{absorbance } (530 \text{ nm} + 590 \text{ nm})$$

where
$I_{Ref}$ = Water reference fluorescence intensity
$I_{Samp}$ = Sample fluorescence intensity (See FIG. 7)
s = Compensation for 30 degree angle of excitation/emission which effectively extends path length, i.e. $\cos \theta = \text{adj/hyp} = 1.1$.

A plot of absorbance vs. concentration should be linear and superimpose the spectrophotometer data which provides direct confirmation of the mathematical description of the method.

Figure 8:
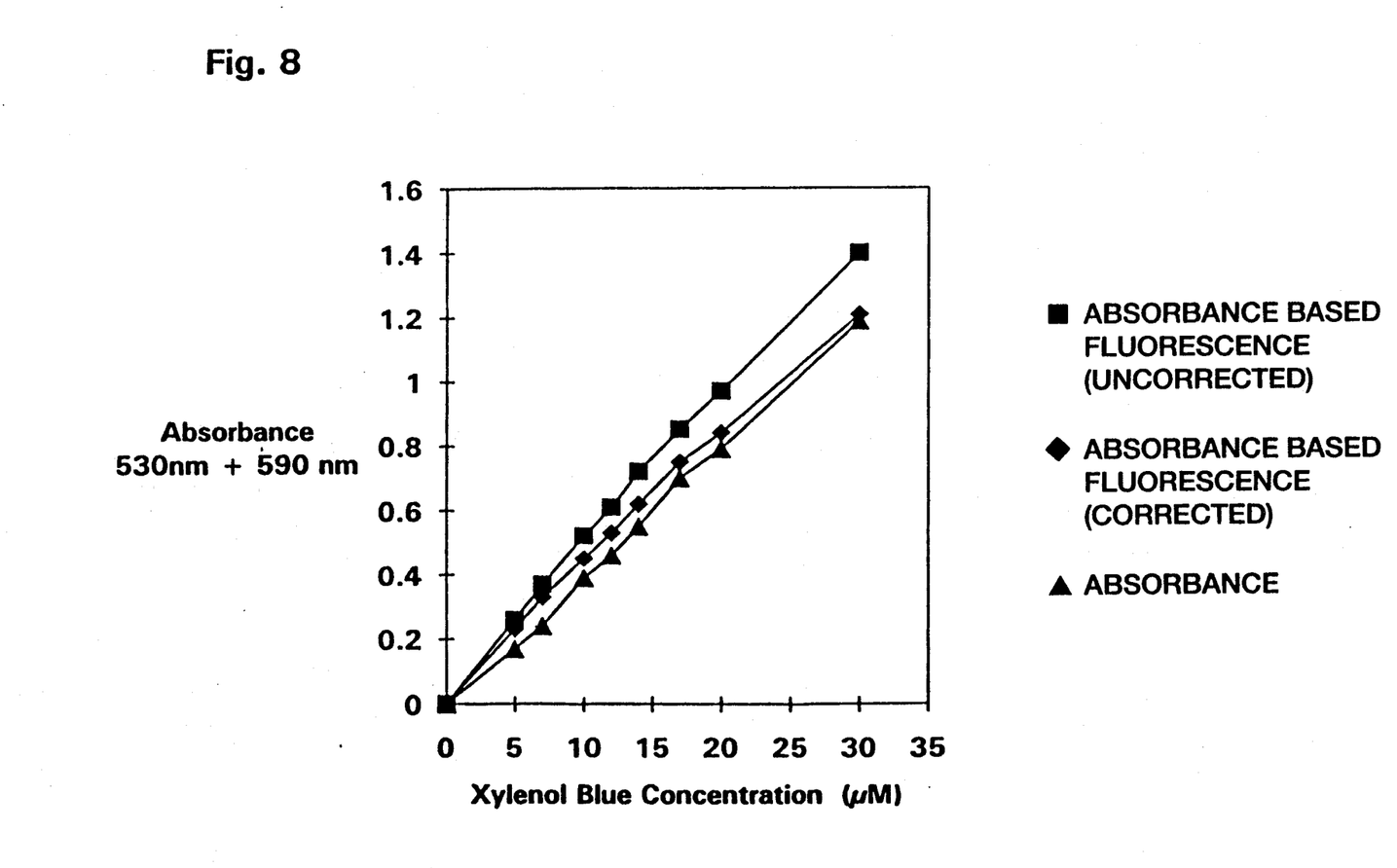
FIG. 8 shows a comparison of indirect vs. direct absorbance measurements.

It is implicit that once the above determinations have been made, any unknown concentration of the same dye may be obtained by using either the plot or direct calculation using the extinction coefficient. See FIG. 8.

The following examples serve to illustrate the method of the present invention. The concentration of reagents and other variable parameters are only shown to exemplify the methods of the present invention and are not to be considered limitations thereof.

EXAMPLE 1

Beta-Lactamase Assay

Beta-lactamase is an enzyme which cleaves a bond in the lactam ring of penicillin. A carboxylic group is generated upon cleavage of the lactam ring. The cleavage destroys the potency of the antibiotic. One method to detect beta-lactamase activity is based on the competition between the open lactam ring and starch for $I_2$ molecules (iodometric). In this assay $I_2$ is the chromogenic reagent. The open lactam ring of penicillin is a compound related product of beta lactamase activity. In the iodometric method, $I_2$ binds noncovalently to starch producing an intense blue-purple color. If an embedded fluorophore is present, then its fluorescence will be reduce. In the presence of beta-lactamase, penicillin G is modified and the $I_2$ binds to the open lactam ring, resulting in a clearing of color from the compartment. As the compartment color clears, the fluorescence increases.

The test was performed as follows:

1. Preparation of the Embedded Fluorophore

Twelve mls of epoxy resin was gently mixed with two mls of hardener for 5–10 minutes taking care not to cause cavitation, four mls of the mixture was then removed and discarded. 7-diethylamino-4-methylcoumarin, DM Coumarin ™ (Molecular Probes) was dissolved in 100% absolute methanol at a concentration of $1.0 \times 10^{-2}$M, and 40 μl was added to the 10 mls of epoxy mixture. The material was mixed for an additional hour, and then 50 μl was dispensed into the wells of a white 96 well tray. This provides an effective vertical path length of 2 mm. This is contrasted with a path length of the aqueous assay of approximately 8 mm.

2. Assay for Beta-lactamase

An inoculum suspension of a bacterial isolate in saline/pluronic, equivalent in turbidity to a 0.5 McFarland turbidity standard was prepared and 300 μl of the bacterial inoculum was added to 25 mls of the Pos Inoculum ™ Broth (Baxter Diagnostics Inc., MicroScan Division). One hundred fifteen μl of this inoculum was added to a reaction well containing 0.8 mg/ml penicillin G (Wyeth Laboratories), 0.2% starch (J. T. Baker), and an epoxy embedded fluorophore. Next 50 μl of the undiluted inoculum of bacterial isolate was added. The mixture was incubated for 5½ hours at 37° C. Finally, 50 μl of 2% Iodine solution (Scientific Products), was added and the mixture was incubated for 10 minutes.

If beta-lactamase is present, then the blue color will fade to clear and the fluorescence will increase.

TABLE 1

| Immobilized fluorophore | Reference | | |
| --- | --- | --- | --- |
| | Positive | Negative | Total |
| Positive | 45 | 1 | 46 |
| Negative | 5 | 86 | 91 |
| Total | 50 | 87 | 137 |
| % Agreement | 131/137 | 95.6% | |
| Sensitivity | 45/50 | 90.0% | |
| Specificity | 86/87 | 98.9% | |

Sensitivity: % correct for cases showing a positive result by the reference method.
Specificity: % correct for cases showing a negative result by the reference method.

The reference method for the beta-lactamase test consists of using MicroScan POS conventional panels (Scientific Products) inoculated and incubated according to the package insert. These conventional overnight results were compared to results obtained in five and one half hours with the method disclosed in Example 1.

EXAMPLE 2

Indole Assay

Indole forms a green-blue colored complex when reacted with dimethylaminocinnamaldehyde at low pH. On formation of this quinoid complex there is a delta increase in absorbance at 365 nm and 450 nm (the fluorophore excitation and emission wavelengths respectively). The increase in absorbance at both wavelengths maximizes the effective total fluorescence change detected; chromogenic reaction product transmissive excitation light and detected emission will decrease. See FIG. 1A, Excitation and/or Emission Based Absorbance Measurements. The resultant decrease in measured fluorescence is related to the amount of indole present. The test was performed as follows:

1. Preparation of Embedded Fluorophore

Six mls of epoxy resin was gently mixed with one ml of hardener for 5-10 minutes taking care not to cause cavitation. It should be noted that this is not the manufacturer's recommended ratio of resin/hardener because it was determined from numerous experiments that the hardener was in excess. The excess hardener remained on the surface of the well interacting with the reaction mixture to produce a false positive. 7-diethylamino-4-methylcoumarin, DM Coumarin TM (Molecular Probes) was dissolved in 100% absolute methanol at a concentration of $1.8 \times 10^{-3}$M, and 65 µl to be added to the curing epoxy mixture. The material was mixed for an additional hour, and then 50 µl was dispensed into the wells of a white 96 well microtiter tray. This provides an effective vertical path length of 2 mm. This is contrasted with a path length of the aqueous assay of approximately 8 mm.

2. Assay for Indole

An inoculum suspension of the bacterial isolate in saline/pluronic, equivalent in turbidity to 0.5 McFarland turbidity standard was prepared and 115 µl of the inoculum was added to a reaction well containing 0.3% Tryptophan (Sigma), 0.1% Bacto-peptone (Difco), and 0.5% $KPO_4$ buffer at pH 7.6, in addition to the epoxy embedded fluorophore. The reaction mixture was incubated for two hours at 35° C. Finally, 75 µl of the chromogenic reagent, dimethylaminocinnamaldehyde in 1.2M HCl was added. The mixture was allowed to react for 10 minutes.

If indole is produced by the isolate, the reaction mixture will turn green. Measurement of fluorescence will show a marked decrease relative to the initial measurement; this change can then be related to the concentration of indole present in the reaction mixture. The present methodology is an improvement over the conventional methodology to test for indole in that required incubation period is about two hours, which is contrasted with the conventional indole test that requires about 24 hours of incubation time.

TABLE 2

| Immobilized Fluorophore | Conventional Method | | |
| --- | --- | --- | --- |
| | Positive | Negative | Total |
| Positive | 61 | 27 | |
| Negative | 6 | 46 | |
| Total | 67 | 73 | |
| % Agreement | 107/140 | 76.4% | |
| Sensitivity | 61/67 | 91% | |
| Specificity | 46/73 | 63% | |

Sensitivity: % correct for cases showing a positive result by the reference method.
Specificity: % correct for cases showing a negative result by the reference method.

The conventional method for the indole test was performed as described in the package insert for the MicroScan GN ID only panel (Scientific Products). The incubation period was overnight.

EXAMPLE 3

Oxidase Assay

In a further embodiment, the principle can be applied to the detection of the enzyme oxidase. The presence or absence of this enzyme is used in identification of both fermentative and non-fermentative bacteria. This test detects the ability of organisms to oxidize the redox dye N,N,N',N'-tetramethyl-p-phenylenediamine in the presence of atmospheric oxygen by observation of a change in the reaction mixture from colorless to blue. If a fluorophore such as 7-methyl-amino-coumarin or 7-diethylamino-4-methyl-coumarin is immobilized in a matrix within the base of the test chamber, its fluorescence will be quenched by the formation of a blue color when the enzyme is present. The greater the intensity of color, the greater the fluorescence attenuation of 7-methyl-amino-coumarin, or diethylamino-4-methylcoumarin.

Procedure

1) Make an inoculum in saline/pluronic of a bacterial isolate equivalent in turbidity to a 0.5 McFarland turbidity standard.
2) Add 50 µl of the inoculum to a chamber having an epoxy embedded fluorophore on its base and dried material equivalent to 2.5 mM,N,N,N',N', tetramethyl-p-phenylenediamine (Sigma), 0.5 mM N-acetylcysteine, 50 mM succinic acid and 50 mM NaOH at pH 6.0. Add 50 µl of saline to a control chamber containing the above ingredients and epoxy embedded fluorophore on its base.
3) Incubate for two hours at 35° C. Measure using front face fluorometry. See FIG. 1A, Excitation and/or Emission Based Absorbance Measurement.
4) For oxidase positive organisms, measurement of the fluorescence will show a marked decrease relative to the control, and related to the oxidized $N,N,N^1,N^1$-tetramethyl-p-phenylenediamine.

Alternatively, the decrease in fluorescence as compared to that at time zero could be indicative of oxidase activity.

EXAMPLE 4

Phenylalanine-ammonia-lyase Assay

In a further embodiment, the principle can be applied to the detection of the enzyme phenylalanine-ammonia-lyase (L-amino acid oxidase, phenylalanine test, deaminase test). The presence of this enzyme has been used for specific recognition of the tribe Proteae and identification of *Moraxella phenylpyruvica*. This test detects the ability of the organisms to deaminate an L-amino acid to form an alpha keto acid+ammonia. Using the synthetic compound p-nitrophenylalanine as the substrate enzyme activity will result in p-nitrophenylpyruvic acid which can be detected, after addition of NaOH, by the appearance of a brownish color. If a fluorophore such as 7-methyl-amino-coumarin or 7-diethylamino-4-methyl-coumarin (DMC) is used, then fluorescence quenching in relation to the amount of p-nitro-phenylpyruvic acid occurs.

The test is performed as follows:

Procedure

1) Make an inoculum in saline/pluronic of a bacterial isolate equivalent in turbidity to a 0.5 McFarland turbidity standard.
2) Add 50 μl of the inoculum to a chamber containing the fluorophore dimethyl coumarin immobilized in its wall and dried material equivalent to 5 mM DL-β-(p-nitrophenyl)-alanine (Koch Light Laboratories), 0.1M Tris(hydroxy-methyl) methylamine, 0.1M $KH_2PO_4$, at pH 8.0. Add 50 μl of saline to a control chamber containing the above ingredients and the fluorophore immobilized in the base of the chamber.
3) Incubate for two hours at 35° C.
4) After incubation, add 25 μl 0.2M NaOH to test and control chambers. If p-nitrophenylpyruvic acid is present, the reaction mixture will turn yellow brown. Measurement of fluorescence will show marked decrease relative to control and related to the p-nitrophenylpyruvic acid present.

EXAMPLE 5

Voges-Proskauer Test

In a further embodiment, the principle can be applied to the detection of Voges-Proskauer (V-P) positive organisms. The V-P reaction, Voges, O. and Proskauer, B. *Beitrag zur Ernahrungsphysiologie und der Differential-diagnose der Bakterien der hamorrhagischen Septicamie* Z. Hyg. Infekt. Kr. 28, 20, 1898, detects the production of acetoin (acetyl-methyl-carbinol) and/or diacetyl (butanedione) from glucose or pyruvic acid. This test is important in separating members of the genera Citrobacter, Escherichia and Salmonella from those of the genera Enterobacter, Klebsiella and Serratia. The test consists of a fluorophore such as esculin, 7-methylamino-coumarin or 7-dimethylamino-4-coumarin, immobilized at the base of a chamber containing dried material equivalent to Na-pyruvate (0.1M), creatine (0.07%), thiamine pyrophosphate (0.26 mM) and phthalate buffer (0.05M) at pH 4.8.

Procedure

A 50 μl aliquot of a bacterial inoculum, equivalent in turbidity to a 0.5 McFarland turbidity standard, is added to the test compartment. A 50 μl aliquot of saline is added to a control compartment.

After two hour incubation at 35° C., 25 μl aliquots of a solution of 2.5% naphthol in 1M NaOH are added to both test and control chambers. A positive reaction is indicated by the appearance of a red color, and a concomitant decrease in fluorescence measured by front face fluorometry. See FIG. 1 Excitation and/or Emission Based Absorbance Measurement.

Further embodiments of the principle may be used in immunoassay techniques, e.g. measurement of activities of a peroxidase conjugated to antibodies in a direct, or sandwich, ELISA assay. Quenching of fluorescence of the fluorophore immobilized in the reaction chamber could be used to detect change in color due to enzyme reacting with the 2,2-azino-di-(3 ethyl benzothiazolin sulfone-6)di ammonium salt substrate.

A similar embodiment could apply to measurement of binding of a nucleic acid probe to which an enzyme molecule is conjugated. The activity of said enzyme is demonstrated by action on a chromogenic substrate releasing a product capable of regulating the fluorescence of an immobilized fluorophore.

It should be understood that the specification and examples are illustrative, but not limitative of the present invention and other embodiments with the spirit and scope of the invention will suggest themselves to those skilled in the art.

What is claimed is:

1. A process to detect the presence of a substance in solution comprising:
   providing a light source emitting a beam forming a transmission light path,
   positioning a solution containing said substance and a chromogenic agent in said light path,
   sandwiching said solution between said light source and an isolated fluorophore embedded in a chemically inert light transmissive matrix so as to intersect said light path, said fluorophore having an excitation spectrum overlapping the absorptive spectrum of a chromophore formed by reaction of said chromogenic agent with said substance being detected, and
   detecting a change in fluorophore emission resulting from light being attenuated or enhanced by the chromophore.

2. A process to determine the concentration of a substance in solution comprising:
   providing a light source emitting a beam forming a transmission light path,
   positioning a solution containing said substance and a chromogenic agent in said light path,
   sandwiching said solution between said light source and an isolated fluorophore embedded in a chemically inert light transmissive matrix so as to intersect said light path, said fluorophore having an excitation spectrum overlapping the absorptive spectrum of a chromophore formed by reaction of said chromogenic agent with said substance being detected, and
   measuring a change in fluorophore emission resulting from light being attenuated or enhanced by the chromophore, and calculating the concentration of said substance by utilizing the proportional relationship between the change in fluorophore emission, the intensity of color formed is said reaction, and the quantity of said substance in solution.

3. A process to detect the presence of a substance in solution comprising:
   providing a light source emitting a beam forming a transmission light path, positioning a solution containing said substance and a chromogenic agent in said light path, sandwiching said solution between said light source and an isolated fluorophore embedded in a chemically inert light transmissive matrix so as to intersect said light path, said fluorophore having an emission spectrum overlapping the absorptive spectrum of a chromophore formed by reaction of said chromogenic agent with said substance being detected, and detecting a change in fluorophore emission resulting from light being attenuated or enhanced by the chromophore.

4. A process to determine the concentration of a substance in solution comprising:

providing a light source emitting a beam forming a transmission light path, positioning a solution containing said substance and a chromogenic agent in said light path, sandwiching said solution between said light source and an isolated fluorophore embedded in a chemically inert light transmissive matrix so as to intersect said light path, said fluorophore having an emission spectrum overlapping the absorptive spectrum of a chromophore formed by reaction of said chromogenic agent with said substance being detected, and measuring a change in fluorophore emission resulting from light being attenuated or enhanced by the chromophore, and calculating the concentration of said substance by utilizing the proportional relationship between the change in fluorophore emission, the intensity of color formed is said reaction, and the quantity of said substance in solution.

* * * * *